(12) United States Patent
Warrick et al.

(10) Patent No.: US 7,659,523 B1
(45) Date of Patent: *Feb. 9, 2010

(54) INTEGRATED ASSEMBLY FOR DELIVERY OF AIR STREAM FOR OPTICAL ANALYSIS

(75) Inventors: Bret R. Warrick, Grants Pass, OR (US); Geoffrey Wilson, Rogue River, OR (US); Richard DeFreez, Azalea, OR (US); Michael M. Carrabba, Rogue River, OR (US)

(73) Assignee: Hach Ultra Analytics, Inc., Grants Pass, OR (US)

( * ) Notice: Subject to any disclaimer, the term of this patent is extended or adjusted under 35 U.S.C. 154(b) by 551 days.

This patent is subject to a terminal disclaimer.

(21) Appl. No.: 11/529,114

(22) Filed: Sep. 28, 2006
(Under 37 CFR 1.47)

Related U.S. Application Data (63) Continuation of application No. 11/062,227, filed on Feb. 18, 2005, now Pat. No. 7,173,257.

(51) Int. Cl.
*G01N 21/64* (2006.01)
(52) U.S. Cl. .................................. 250/458.1
(58) Field of Classification Search ............... 250/458.1
See application file for complete search history.

(56) References Cited

U.S. PATENT DOCUMENTS

| | | | |
|---|---|---|---|
| 3,754,868 A | 8/1973 | Witz et al. | 23/254 |
| 4,133,202 A | 1/1979 | Marple | 73/28 |
| 4,972,957 A | 11/1990 | Liu et al. | 209/143 |
| 5,674,200 A * | 10/1997 | Ruschke et al. | 604/126 |
| 5,701,012 A | 12/1997 | Ho | 250/461.2 |
| 5,788,741 A | 8/1998 | Burton et al. | 95/32 |
| 5,932,795 A | 8/1999 | Koutrakis et al. | 73/28.01 |
| 6,111,642 A | 8/2000 | DeFreez et al. | 356/337 |
| 6,289,751 B1 | 9/2001 | Mathur et al. | 73/863 |
| 6,431,014 B1 | 8/2002 | Liu et al. | 73/863.22 |
| 6,478,856 B1 | 11/2002 | Leiholz et al. | 95/266 |
| 6,520,034 B1 | 2/2003 | Masqueller et al. | 73/863.21 |
| 6,619,143 B2 | 9/2003 | Danylewych-May et al. | 73/863.21 |
| 6,639,671 B1 | 10/2003 | Liu | 356/336 |
| 6,688,187 B1 | 2/2004 | Masqueller | 73/863.22 |
| 6,729,196 B2 | 5/2004 | Moler et al. | 73/863.22 |
| 6,777,228 B2 | 8/2004 | Lejeune | 435/309.1 |
| 6,829,919 B2 | 12/2004 | Sioutas et al. | 73/28.04 |

(Continued)

OTHER PUBLICATIONS

Luoma, et al. "A Fluorencent Particle Detector for Real Time Quantification of Viable Organisms in Air", Proceeding of SPIE, vol. 4576 (2002).

(Continued)

*Primary Examiner*—Constantine Hannaher
(74) *Attorney, Agent, or Firm*—Stoel Rives LLP; Matthew S. Bethards (57) ABSTRACT

An integrated particle detection apparatus for optical detection of particles in an air stream. The particle detection apparatus includes a scalper for removing large particles from the air stream, a concentrator for separating out small particles and increasing the concentration of particles of interest, and a fluorescence sensor system for detecting the particles present in the air stream. The scalper, concentrator and sensor may include a single integrated unit, such that the scalper is fluidly contiguous with the concentrator and the concentrator is fluidly contiguous with the sensor.

11 Claims, 7 Drawing Sheets

U.S. PATENT DOCUMENTS

| | | | |
|---|---|---|---|
| 7,173,257 B1* | 2/2007 | Warrick et al. | 250/458.1 |
| 2003/0054558 A1 | 3/2003 | Kurabayashi et al. | |
| 2003/0230152 A1 | 12/2003 | McGill et al. | 73/864.34 |
| 2004/0025604 A1 | 2/2004 | Call et al. | 73/863.22 |
| 2004/0043443 A1 | 3/2004 | Lejeune | 435/29 |
| 2005/0070025 A1 | 3/2005 | Mooradian et al. | 436/178 |

OTHER PUBLICATIONS

Mesosystems, Micro Vic Particle Concentrator (2004) Product Brochure, No Month.

National Research Council, "Sensor Systems for Biological Agent Attacks: Protecting Buildings and Military Bases." (2005) The National Academies, Washington D.C. (Ch 4&5) http://www.nap.edu/catalog/11207.html.

Wilson, et al. "Advances in BioLert Diode Laser Based Laser Induced Fluorescence Bio-particle Sensors", (Sep. 14, 2004) Hach Ultra Analytics.

Wilson, et al., "Multispectral Diode Laser Induced Fluorescence Biological Partical Sensor", Optically Based Biological and Chemical Sensing for Defence, Proceedings of SPIE vol. 5617 (SPIE, Bellingham, WA, 2004) (Published after Oct. 25, 2004).

* cited by examiner

INTEGRATED ASSEMBLY FOR DELIVERY OF AIR STREAM FOR OPTICAL ANALYSIS

CROSS-REFERENCE TO RELATED APPLICATIONS

This application is a continuation of U.S. Nonprovisional patent application Ser. No. 11/062,227, entitled Integrated Assembly For Delivery of Air Stream For Optical Analysis, filed Feb. 18, 2005 now U.S. Pat. No. 7,173,257, now pending, which is hereby incorporated by reference.

FEDERALLY SPONSORED RESEARCH OR DEVELOPMENT

Work on this invention was carried out under Defense Advanced Research Projects Agency ("DARPA") Microsystems Technology Office contract No. N66001-02-C-8016 in support of a program entitled Semiconductor Ultraviolet Optical Sources ("SUVOS"). The government has certain rights in the invention.

TECHNICAL FIELD

This invention relates to particle detection systems and, in particular, to pre-filter, concentrator and sensor assemblies for providing sample preparation and delivery for optical particle detection.

BACKGROUND OF THE INVENTION

Contamination control, including particulate monitoring, plays a role in the manufacturing processes of several industries. These industries require clean rooms or clean zones with active air filtration and require the supply of clean raw materials such as process gases, de-ionized water, chemicals, and substrates. In the pharmaceutical industry, the Food and Drug Administration requires particulate monitoring because of the correlation between detected particles in an aseptic environment and viable particles that contaminate the product produced.

Recent attention has been given to the monitoring and detection of biological agents. If aerosolized agents (biological particles) are introduced into an environment and are within the respirable range of particle sizes, then the biological particles may deposit in human lungs resulting in illness or death.

Biological contamination can occur not only in open air, but also in confined spaces, such as postal handling equipment, aircraft, hospitals, water supplies, and air ducts. Minimizing the introduction of biological particles in an environment requires the fast detection of pathogens. Laser-induced fluorescence ("LIF") of fluorescent biological substances (biofluorophores) provides a real-time technique for identifying the potential presence of airborne pathogens such as aerosolized bacterial spores and viruses. Biofluorophores significant to LIF include, but are not limited to, tryptophan, NADH, and riboflavin or other flavinoids.

Assemblies that have been used in the detection of particles include pre-filter scalpers, concentrators and LIF sensors. The scalper and concentrator may be used to separate out undesirable particles and supply the air stream sample to an LIF sensor in a manner conducive to LIF detection. A scalper in this context may be a device used to separate out particles in the sample air stream, for example, based on particle size. A scalper may be used to remove large particles from the sample air stream. A concentrator may be used to increase particle concentration by increasing the number of particles by volume in the sample air stream.

Traditional implementations of LIF sensor systems use a separate scalper and a separate concentrator to prepare the sample air stream and provide particles to the LIF sensor. The separate scalper, concentrator and sensor assemblies were often bulky, which can be a disadvantage. For example, the allowable space for the detection system may be limited when the sample air stream is in an environment such as air ducts. Furthermore, tubing is required to interconnect the scalper and the concentrator with the LIF sensor. Tubing has a tendency to trap particles of interest, which frequently results in fewer particles entering the sensor.

Furthermore, in traditional LIF sensors, the sample sensor compartment where the sample stream and the incident excitation beam meet is often difficult to access. Typically, the only way to clean the sample sensor compartment is by accessing it through the various module ports, resulting in poor access to the interior surfaces that require cleaning. Furthermore, to access the interior sample sensor compartment through the ports requires the removal of either the laser module, the elastic scatter device, the photodetector device or the dispersive fluorescence detector device.

Therefore, it would be an advancement in the art to address one or more of these problems. It would also be desirable to provide an apparatus that is less bulky than previous implementations.

SUMMARY OF THE INVENTION

The embodiments disclosed have been developed in response to the present state of the art, and in particular, in response to the problems and needs in the art that have not yet been fully solved by currently available particle detection systems. According to one embodiment, an integrated air stream delivery apparatus suitable for use with a system for performing analysis based on optical illumination of a sample air stream is provided. The delivery apparatus has a scalper portion, a concentrator portion and an illumination area that make up a single integrated unit and are also in fluid communication with each other.

The scalper portion can separate particles within the air stream based on particle size. The concentrator portion can alter the concentration of particles that are within the sample air stream. The illumination area may receive the sample air stream from the concentrator portion. The illumination area may be configured to receive illumination from a light source for illuminating the sample air stream.

The scalper, concentrator and illumination area may be defined by a housing. The housing may define passageways through which the sample flows between the scalper portion, concentrator portion and illumination area. The apparatus may include a flow manifold where flow passages are integrated in the housing. The housing may also be made of removable pieces, such as two housing portions, for providing access to the interior of the scalper portion, concentrator portion and illumination area. A sealing member or gasket may also be included to provide a seal when the housing portions are joined together.

The apparatus may also include a sample nozzle for delivering the sample air stream to the illumination area. The position of the sample nozzle within the housing may be adjustable from outside the housing. A sheath nozzle may also be machined or otherwise formed in the housing and be concentric with the sample nozzle.

According to one embodiment, the scalper portion may remove some or all particles from the sample air stream that are larger than a defined maximum size limit, such as about 10 microns in diameter. Furthermore, the concentrator portion may increase the concentration, or number of particle by volume, within the sample. The concentrator portion may also remove from the sample particles that are smaller than a defined minimum size limit, such as about one micron in diameter.

The illumination area may include a chamber, at least one port for receiving a light source and at least one port for receiving an optical detector. The apparatus may also include at least one optical detector, such as a fluorescence detector. Alternatively or in combination, at least one optical detector may be an elastic scatter detector, a laser power detector, and an obscuration detector. The light source may be a laser light source or it could be a light emitting diode.

Additionally a particle detection apparatus for detecting particles in a sample air stream is disclosed. The particle detection apparatus may include a scalper, a concentrator and a sensor, wherein the scalper is fluidly contiguous with the concentrator and the concentrator is fluidly contiguous with the sensor. The concentrator may be configured to increase the concentration of particles within the sample air stream. The sensor may be configured to detect particles.

The sensor may be an induced fluorescence sensor system. The fluorescence sensor system may include a light source, a fluorescence detector, a light source power detector and an elastic scatter detector. The light source may be a laser-light source or alternatively, the light source may be a light emitting diode. The light source may be adjustable in all directions along a mounting plane.

According to yet another embodiment, a particle detection apparatus for detecting particles in a sample air stream may include a scalper, a concentrator, a sample sensor compartment where fluorescence of sample particles occur, and a housing. The scalper, concentrator, and sample sensor compartment may be in fluid communication with each other and are defined by the housing.

These and other features and advantages of the disclosed embodiments will become more fully apparent from the following description and appended claims, or may be learned by the practice thereof as set forth hereinafter.

BRIEF DESCRIPTION OF THE DRAWINGS

The present embodiments will become more fully apparent from the following description and appended claims, taken in conjunction with the accompanying drawings. Understanding that these drawings depict only typical embodiments and are, therefore, not to be considered limiting of the invention's scope, the embodiments will be described with additional specificity and detail through use of the accompanying drawings in which:

DETAILED DESCRIPTION

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the invention, as claimed, but is merely representative of the embodiments of the invention.

The word "exemplary" is used exclusively herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, and thermal interaction. Two components may be coupled to each other even though they are not in direct contact with each other.

The phrase "attached directly to" refers to a form of attachment by which the attached items are either in direct contact, or are only separated by a single fastener, adhesive, or other attachment mechanism. The term "abutting" refers to items that are in direct physical contact with each other, although the items may not necessarily be attached together.

Figure 1:
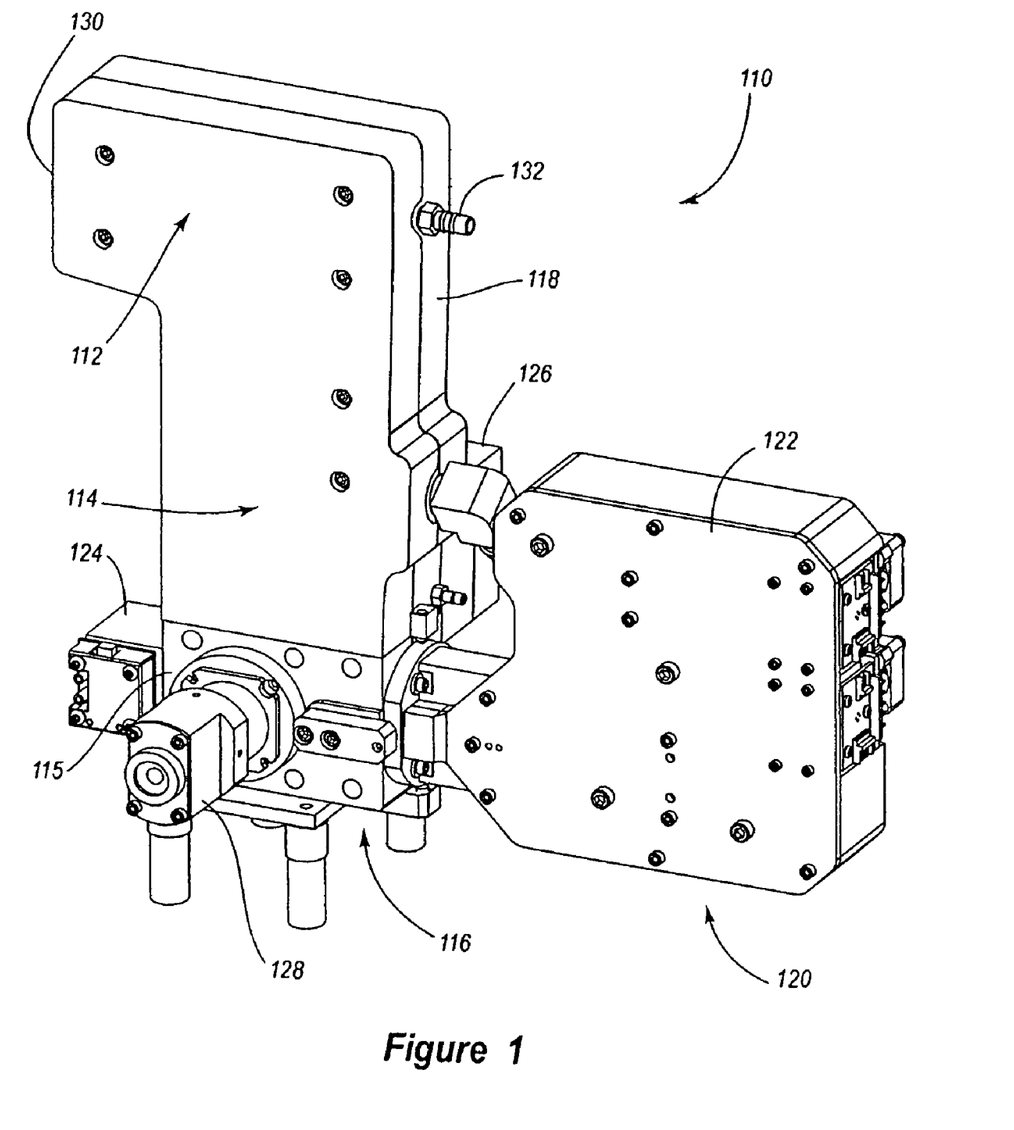
FIG. 1 is perspective view of one embodiment of an integrated particle detection apparatus for detecting particles in a sample air stream including an LIF sensor system.

FIG. 1 represents one embodiment of an integrated air stream delivery apparatus, particularly a particle detection apparatus 110 for detecting particles in a sample air stream as illustrated from a perspective view. The air stream may be a stream of any appropriate carrier gas. The particles may be solid, liquid (such as droplets), or other phases of matter or combinations thereof. The apparatus may be used for analysis of the air stream, the particles, or both.

The particle detection apparatus 110 illustrated includes a scalper 112, a concentration-changing portion ("concentrator") 114, and a sensor system 116. The particle detection apparatus 110 is formed from a housing 118, which may be constructed via an injection molded process. Alternatively, the housing 118 may be machined to provide aerodynamically smooth internal surfaces. Moreover, the housing 118 may also be constructed through a die cast process or other construction process known to those having skill in the art. According to one embodiment, the housing 118 is composed of aluminum. Alternatively, the housing 118 could be composed of other metals, metal alloys, polymers or other suitable material.

According to the embodiment illustrated in FIG. 1, the housing 118 defines the scalper 112, concentrator 114, and a sample sensor compartment that is disposed within an illumination area or sensor body 115. In other words, the scalper 112, the concentrator 114, and sample sensor compartment are formed into the housing so all three comprise an integrated unit. The sample sensor compartment is where fluorescence occurs when the excitation source illuminates the sample air stream, including any particles therein. Consequently, the scalper 112 is not a separate component, but rather an integrated part of the housing 118, and as such could be referred to as a scalper portion 112. The concentrator 114 is also defined by and is an integrated part of the housing 118, and could be referred to as a concentrator portion 114. The sensor body 115 is also defined by and is an integrated part of the housing 118 and could be referred to as the sensor body portion 115.

According to the embodiment illustrated, the sensor system 116 includes a light source 120. The light source 120 may be a laser-light source and the sensor system 116 may be an LIF sensor system. The laser-light source could be a conventional blue, violet, or ultraviolet ("UV") diode laser, a frequency-tripled or quadrupled neodymium laser, or other laser-light source known to those having skill in the art. Alternatively, the light source 120 may be a light emitting diode ("LED") or other light source which can be used to illuminate the air stream for appropriate detection.

According to the embodiment illustrated in FIG. 1, the laser-light source 120 is a dual diode laser beam combining module. This laser module 120 combines two diode laser beams of different wavelengths into a single beam. The wavelengths generated may be, for example, 375 nanometers and 405 nanometers. However the laser module 120 may accommodate other wavelengths as desired. The laser module 120 may be encased in a dust and light-tight cover 122. The apparatus 110 may also accommodate single illumination sources, different combined illumination sources, uncombined multiple illumination sources, or combinations thereof, which sources may be lasers, light emitting diodes, or other sources.

The LIF sensor system 116 also may include a laser power detector 124 on the opposite side of the sensor body 115 from the laser module 120. The laser power detector 124 may be used for measuring the laser power or energy leaving the optical train of the laser module 120. The laser power detector 124 may be used as a relative reference of laser power for spectrum normalization so that the laser power fluctuation does not affect measurement accuracy.

The LIF sensor system 116 also includes a dispersive fluorescence detector 126, which is typically located normal to the excitation beam. A variety of fluorescence detectors 126 may be used, including, but not limited to photomultiplier tubes ("PMTs") in analog or photon-counting mode, diode arrays and charge-transfer detectors. One having skill in the art would recognize that various forms of transducers may be used that provide large amplifier gains to measure low intensity fluorescence signals.

The illumination area 115 may include ports which receive, or which are in optical communication with optical detectors. Multiple detectors may also be used with different filters to measure fluorescence emission at varying wavelengths. Alternatively, a single detector may be used in which all the fluorescence spectral bands share a common aperture and are then dispersed onto a single multiple-pixel detector using a diffraction grating. In the latter system a long-pass filter may be included to block stray laser light at the excitation wavelength.

The detectors may also include other types of detectors, for instance, to detect or measure extinction or obscuration of an illumination source, or scatter, fluorescence, color, or other optically detectable information about the particles and/or air stream. They may include, for instance, photon counters, photomultipliers, charge-coupled devices, or spectrophotometers. They may also include one or more filters, polarizers, or other devices that affect the properties of the detected illumination.

The LIF sensor system 116 may also include an elastic scatter detector 128. Information from an elastic scatter signal can be used in combination with fluorescence intensity information from the fluorescence detector to develop information that is different from the fluorescence intensity signal alone. For instance, the information from both detectors may be used to calculate a fluorescence-to-elastic scatter ratio (F/E) which takes account of particle size. The ratio may also be normalized so that it has a finite domain (for instance from −1 to +1) instead of an infinite domain (such as 0 to infinity). Elastic scatter information may also help to distinguish interferent particles with fluorescence properties similar to pathogens, but with different size distributions. Elastic scatter information also can gate the counting of fluorescence photons.

Referring still to FIG. 1, particle-laden air flows into the particle detection apparatus inlet 130 and through the scalper portion 112. The scalper 112 may remove particles that exceed a maximum size limit, such as particles that are larger than about 10 microns in diameter. Alternatively, the scalper 112 may be configured to remove differently-sized particles. The larger particles that are stripped off exit the scalper portion 112 through a scalper's minor exhaust 132. According to the embodiment shown in FIG. 1, the scalper 112 is a virtual impactor that separates particles by size into two air streams. However, alternative scalper devices may be used as known to those having skill in the art, such as a cyclone device.

Flow of the sample air stream continues from the scalper 112 to the concentrator 114. The concentrator 114 functions to increase the number of particles within a respirable range (approximately 1 to 10 microns) by volume, i.e., increase particle concentration. However, a concentrator could also be used to dilute the concentration of particles in a sample, if desired. The concentrator 114 used in the embodiment shown in FIG. 1 may increase the particle concentration by a factor of about ten. The concentrator 114 also separates out particles smaller than a defined minimum size limit, such as particles smaller than about one micron in diameter. The smaller particles exit the particle detection apparatus 110 through a concentrator exhaust 134 along with much of the air of the sample stream. Like the scalper 112, the concentrator 114 illustrated is a virtual impactor. Also like the scalper 112, alternative devices may be used as known to those having skill in the art, such as a cyclone device.

The remaining particles in the sample air stream, such as those in the 1 to 10 micron range (often referred to as the "respirable range"), continue through a sample nozzle (not shown). The particles then flow from the sample nozzle into the sample sensor compartment and into a view volume within the sensor body 115, that is part of the LIF sensor system 116. The particles are then interrogated by the fluorescence excitation beam generated by the laser module 120. After fluorescence detection occurs, the sample air stream flows out of the integrated particle detection apparatus 110 through a sensor exhaust (not shown).

Figure 2:
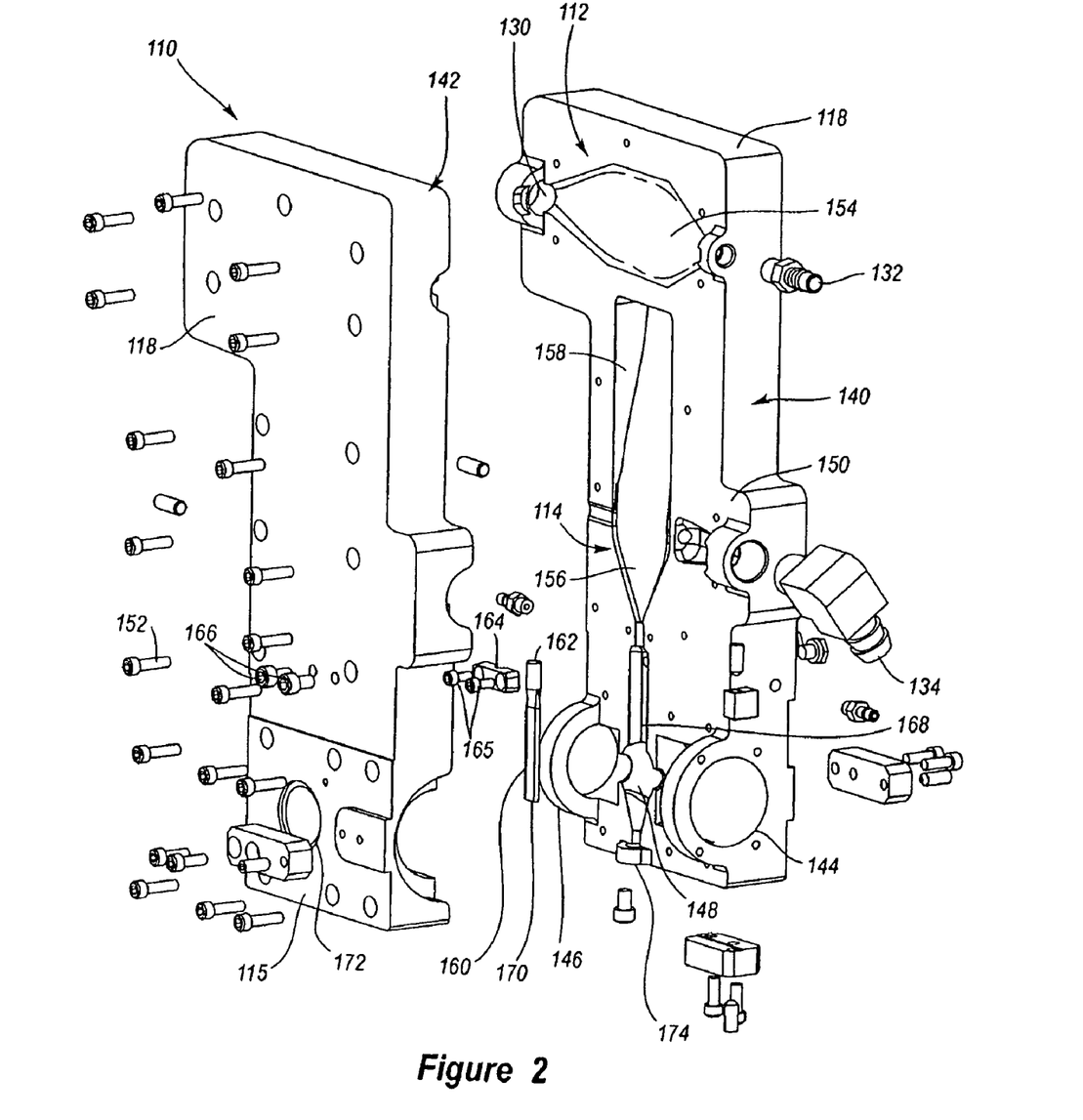
FIG. 2 is an exploded perspective view of the integrated particle detection apparatus of FIG. 1 absent some of the LIF sensor components.

FIG. 2 illustrates the integrated particle detection apparatus 110 represented in FIG. 1, but from an exploded perspective view. The particle detection apparatus 110 depicted in FIG. 2 is illustrated absent the LIF sensor components such as the laser module, dispersive fluorescence detector, laser power detector, and elastic scatter detector. Consequently, the particle detection apparatus 110 may also be considered a particle delivery apparatus 110 for delivering particles to a location where optical detection of particles may occur.

As shown in FIG. 2, the housing 118 of the particle detection apparatus 110 may have a clamshell design forming two portions 140, 142, one of which is fixed and one of which is removable. A fixed portion 140 may be configured to be fixedly coupled, or attached directly to a UV-LIF bio-aerosol sensor instrument assembly (which may include, among other things, flow meters, a pump, a blower, filters, fans, a power supply, and a printed circuit board stack) or frame thereof. A removable portion 142 may be connected to the fixed portion 140, but could be easily removed to provide access to the interior of the particle detection apparatus 110 for cleaning or servicing. This is advantageous over previous "one-piece" sensor assemblies because the only access to cleaning one-piece sensors is through module ports, resulting in poor access to surfaces that should be kept clean.

In the embodiment shown in FIG. 2, the two housing portions 140, 142 split the integrated particle detection apparatus 110 approximately in half longitudinally and widthwise. Therefore, approximately half of the scalper 112, half of the concentrator 114, and half of the sensor body 115 are found on the fixed half 140, while half of the scalper 112, half of the concentrator 114, and half of the sensor body 115 are formed on the removable half 142. The term "half" is not intended to mean exactly 50% by size or weight. Rather, two halves in this context mean that each half has a similar size as the other half. For example, a laser module port 144 may be formed in the fixed half 140, but not the removable half 142 so that laser module removal is not necessary when the removable half 142 is taken off for cleaning. A laser power detector port 146 also may be formed in the fixed half 140 so that the laser power detector (not shown) does not need to be removed when the removable half 142 is removed. Alternatively, the housing 118 may be formed from a fixed portion 140 and a removable portion 142 which are not similar in size.

FIG. 2 also shows a sample sensor compartment 148 where fluorescence occurs when the excitation source interrogates the sample stream. The sample sensor compartment 148 could also be considered part of the illumination area where the sample particle stream is delivered from the concentrator 114. Approximately half of the sample sensor compartment 148 is located on the fixed half 140 of the particle detection apparatus 110, while the other half is located on the removable half 142 of the detection apparatus 110.

The two halves 140, 142 each have a mating surface 150 which abut each other when placed in a closed configuration (as shown in FIG. 1). The two halves 140, 142 may be coupled to each other through the use of fasteners, such as cap screws 152. Alternative fasteners and fastening methods may be used such as clamps, which may speed disassembly of the particle detection apparatus 110.

Particle-laden air flows into the particle detection apparatus inlet 130 and into a scalper chamber 154 of the scalper portion 112. As discussed previously, the scalper 112 may remove particles in the air stream that exceed a maximum size limit, such as particles that are larger than about 10 microns. The larger particles that are stripped off exit the scalper 112 through the scalper exhaust 132.

Flow of the sample air stream continues from the scalper 112 to a concentrator cavity 156 via passageway 158. The concentrator 114 separates out particles smaller than a minimum size limit and increases the concentration of particles in the respirable range. The smaller particles exit the particle detection apparatus 110 with a majority of the air flow through the concentrator exhaust 134. Alternatively, the scalper 112 may be located downstream of the concentrator 114.

The remaining particles in the sample air stream (e.g., those in the 1 to 10 micron range) enter into a sample nozzle 160 through its upper end 162. The upper end 162 of the sample nozzle 160 may have a round cross-section and is machined to provide a smooth transition for the particle-laden flow as it exits the concentrator 114 and enters the sample nozzle 160. According to one embodiment, the sample nozzle 160 is constructed from steel tubing. The cross-section of the nozzle 160 is round at its upper end 162 and then transitions to an elliptical or "racetrack"-shaped cross section. The elongated shape of the sample nozzle 160 delivers the sample in a configuration that maximizes fluorescence efficiency due to the shape of the laser beam source. Flow through the sample nozzle 160 may be laminar. However, laminar flow is not required; in alternative embodiments flow to the illumination area or out of the sample nozzle 160 could be turbulent.

The sample nozzle 160 may be coupled to the fixed half 140 of the particle detection apparatus 110 through the use of a sample nozzle clamp 164. According to the embodiment illustrated in FIG. 2, the sample nozzle clamp 164 is shaped to pinch the upper end 162 of the sample nozzle 160 without crushing it and/or restricting the particle-laden flow. The sample nozzle clamp 164 may be tapered around its perimeter to seal it to the removable half 142 of the particle detection apparatus 110 when the two halves 140, 142 are in the closed configuration.

The sample nozzle clamp 164 can be loosened through nozzle clamp screws 165 and the position of the sample nozzle 160 can be adjusted thereby. The nozzle clamp screws 165 may be accessible even when the two halves 140, 142 are in the closed configuration by removing nozzle clamp access screws 166 that are exposed on an exterior of the housing 118. Once the nozzle clamp access screws 166 are removed, the nozzle clamp screws 165 can then be accessed to loosen or tighten the sample nozzle clamp 164 as desired. Consequently, the position of the sample nozzle 160 within the housing 118 may be adjusted by an operator from outside of the housing.

The integrated particle detection apparatus 110 may also include a sheath nozzle 168 that is integrated into the housing 118. Previous implementations of particle detection systems required the use of a separate formed tube for the sheath nozzle. According to the present embodiment, the sheath nozzle 168 may be machined into the housing 118 concentric with the location of the sample nozzle 160, such that it encompasses the sample nozzle 160. Clean air from the sheath nozzle 168 flows around the sample nozzle 160 and helps control the shape of the particle-laden flow as it exits the sample nozzle 160 at its lower end 170. The clean flow from the sheath nozzle 168 also may help prevent optical surfaces from being coated with particles.

Once the particle-laden sample air stream has exited the sample nozzle 160 it enters into the sample sensor compartment 148 where the sample is irradiated by the excitation beam and fluorescence detection occurs. The removable half 142 of the particle detection apparatus 110 may include an elastic scatter detector port 172 where the elastic scatter detector (not shown) may be coupled to measure elastic scatter during fluorescence analysis. After fluorescence detection occurs, the sample air stream flows out of the integrated particle detection apparatus 110 through a sensor exhaust 174.

Figure 3:
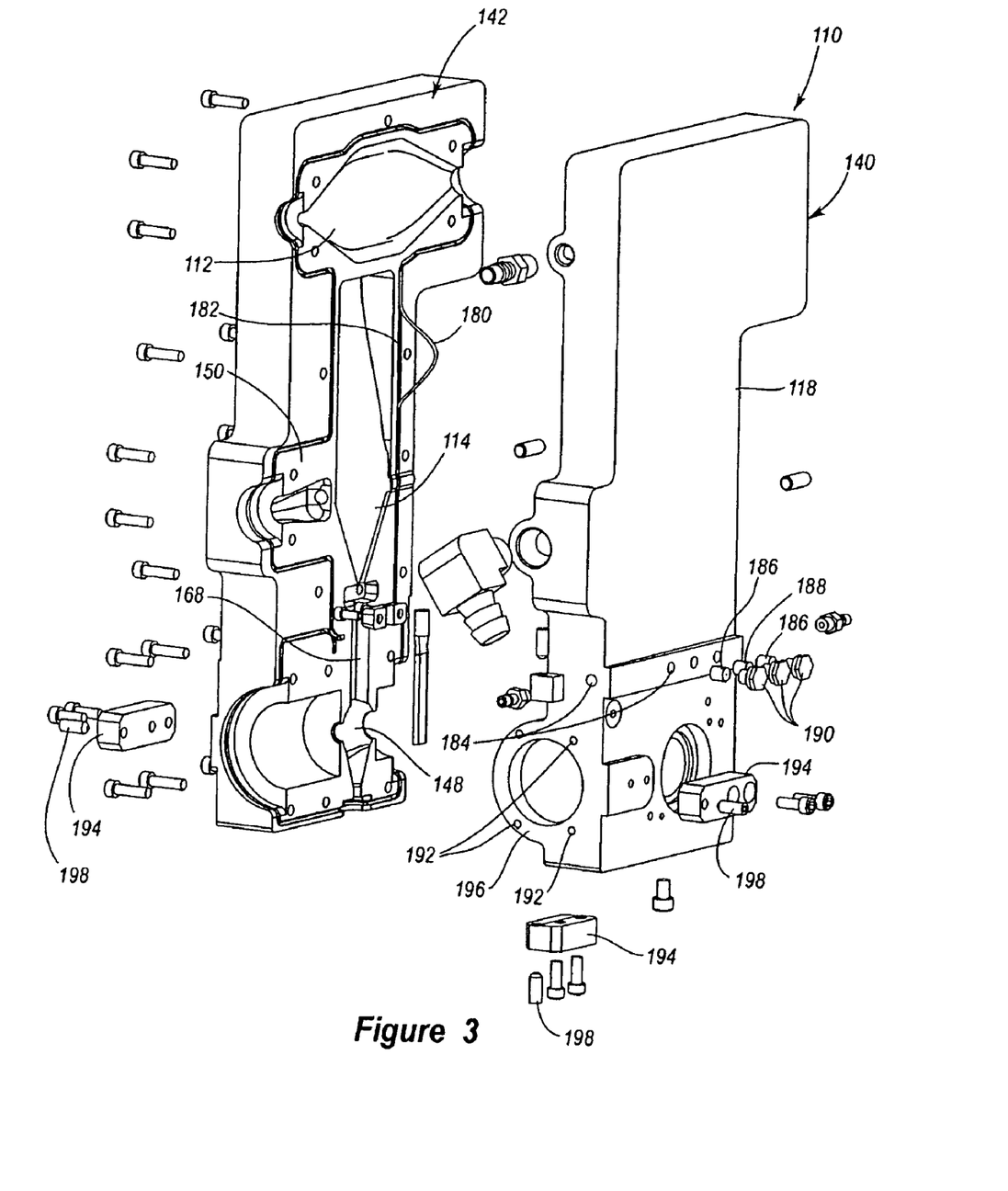
FIG. 3 is an exploded perspective view of the integrated particle detection apparatus of FIG. 2 as shown from an alternative angle.

FIG. 3 illustrates the integrated particle detection apparatus 110 represented in FIG. 2, but from an alternative angle of an exploded perspective view. FIG. 3 illustrates the interior portion of the removable half 142 of the particle detection apparatus 110 including the other half of the scalper 112, concentrator 114, sheath nozzle 168 and sample sensor compartment 148.

When in use, the two halves 140, 142 of the particle detection apparatus 110 are in the closed configuration (as shown in FIG. 1). In the closed configuration the mating surface 150 of the removable half 142 typically abuts the mating surface of the fixed half 140. It is desirable for the abutting mating surfaces 150 to form a seal so that the particle detection apparatus 110 can build up air pressure in the interior cavities. Although it could be, the seal does not necessarily need to be hermetic. Rather, the seal may be such that the particle detection apparatus 110 can build up air pressure in its interior cavities.

The abutting mating surfaces 150 typically do not provide a sufficient seal through bolt pressure alone because of the many features on the mating surface 150. Consequently, the mating surface 150 may include a sealing member, such as a sealing gasket 180 or O-ring cord that extends around the perimeter of the removable half 142. The sealing gasket 180 may be pressed or otherwise disposed in a sealing groove 182 that extends around the perimeter of the removable half. Alternatively, the sealing member 180 may extend around the fixed half 140.

According to the embodiment shown in FIGS. 2 and 3, the mating surface 150 of the fixed half 140 is flat and does not have a sealing groove 182. The sealing gasket 180 may have a diameter slightly larger than the width of the sealing groove 182, such that the sealing gasket 180 protrudes slightly out of the groove 182 to form a seal when the removable half 142 is secured to the fixed half 140. The sealing gasket 180 may then remain in the sealing groove 182 when the two halves 140, 142 are separated. The sealing groove 182 may be disposed around all the features in the perimeter of the removable half 142, such as the inlet 130, concentrator exhaust 134, etc.

Since the mating surfaces 150 of the two halves 140, 142 of the particle detection apparatus 110 typically abut each other, the sealing gasket 180 may have a cross-sectional area that is slightly less than the cross-sectional area of the sealing groove 182 so that the sealing gasket 180 can compress in the groove 182 and the two halves 140, 142 are not held apart by the sealing gasket 180.

Referring still to FIG. 3, the fixed half 140 has multiple flow manifold ports 184, some of which receive a purge flow orifice 186 or a sheath flow orifice 188. The purge and sheath flow orifices 186, 188 may screw into threaded features (not shown) on the interior of the flow manifold to control the sheath and purge flow. Flow manifold plugs 190 may also be received by the flow manifold ports 184. Purge and sheath flow will be discussed in greater detail in conjunction with FIGS. 4A through 5D.

The fixed half 140 of the particle detection apparatus 110 may also include laser module attachment locations 192 where the laser module (of FIG. 1) may be coupled to the housing 118. Laser module adjustment plates 194 may be coupled to the side and base of the housing 118 to allow the laser module (of FIG. 1) to be moved in all directions along a mounting plane 196. Alignment of the laser module may be accomplished using set screws 198 mounted on the laser module adjustment plates 194. The adjustability of the laser module in all directions along the mounting plane 196 may be desirable in the event the sample nozzle 160 is adjustable in a vertical direction only.

Figure 4A:
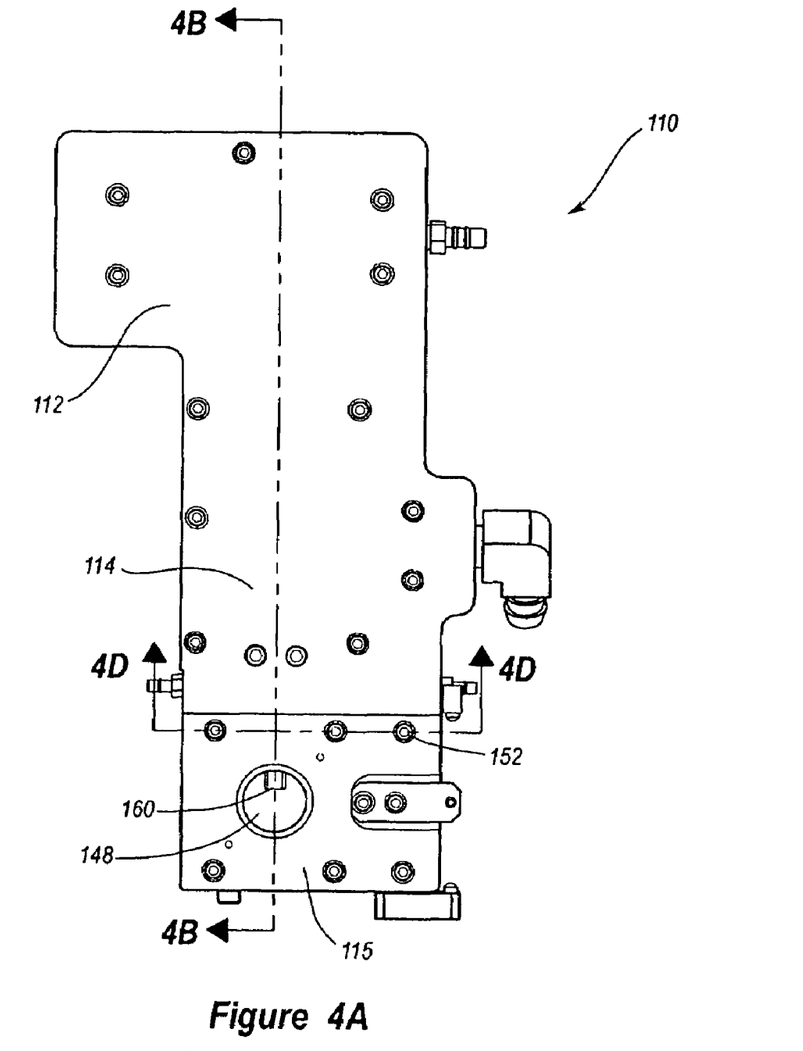
FIG. 4A is a side elevation view of the integrated particle detection apparatus of FIG. 1 absent some of the LIF sensor components.

FIG. 4A illustrates the integrated particle detection apparatus 110 of FIG. 1 from a side elevation view. As discussed previously, the particle detection apparatus 110 includes the scalper 112, the concentrator 114 and the sample sensor body 115. The sample sensor body 115 illustrated in FIGS. 4A through 5D is shown absent its sensor components such as the laser module and various detectors. The scalper 112, concentrator 114 and sensor body 115 form an integrated unit, such that the scalper 112 is fluidly contiguous with the concentrator 114, and the concentrator is fluidly contiguous with the sample sensor body 115. This eliminates the need for air supply tubes and fittings.

Furthermore, the integrated design reduces the number of parts compared to known designs, which results in lower cost and less complexity as previous designs. Moreover, integrating flow system components such as orifices (not shown) into the particle detector apparatus 110 also reduces system complexity.

Figure 4B:
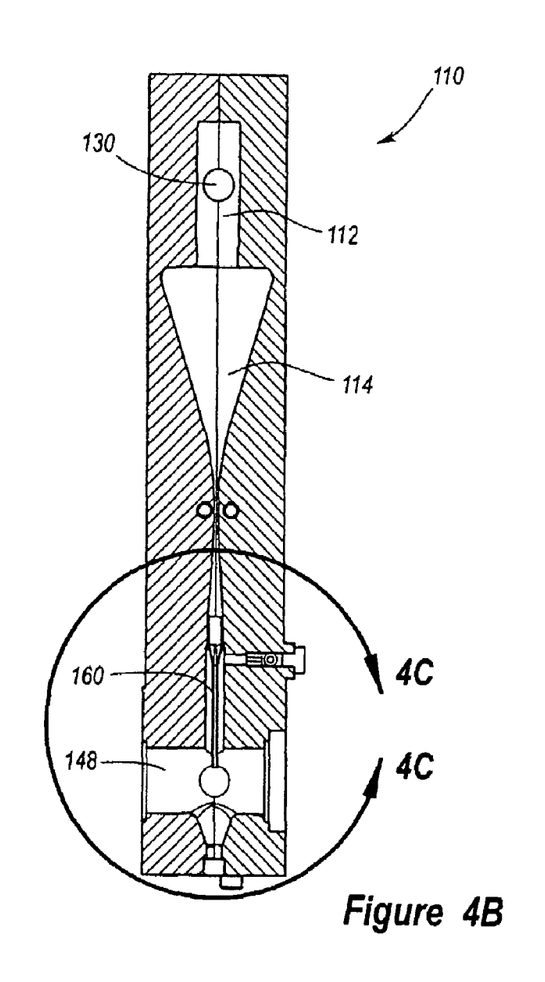
FIG. 4B is a cross-sectional side elevation view of the integrated particle detection apparatus of FIG. 4A as viewed from the cross-sectional plane 4B-4B.

Plane 4B-4B extends through the length and depth of the particle detection apparatus 110 and passes through the scalper 112, the concentrator 114, the sample sensor compartment 148, the sample nozzle 160, the sheath nozzle (not shown) and a sheath flow orifice (not shown). Plane 4D-4D extends through the width and depth of the particle detection apparatus 110 and passes through the internal sample and sheath nozzles (not shown) and cap screws 152.

Referring to FIG. 4B, the particle detection apparatus 110 of FIG. 4A is illustrated from a side cross-sectional view along the plane 4B-4B. The particle-laden air flows into the scalper 112 through the inlet 130, where particles that exceed a maximum size limit are removed. The sample air stream then flows into the concentrator 114 since the scalper 112 and concentrator 114 are fluidly contiguous. According to this embodiment, the concentrator 114 increases the respirable-range particle concentration and separates out particles smaller than a minimum size limit.

The remaining particles in the sample air stream are then delivered to the sample nozzle 160 which in turn delivers the sample air stream into the sample sensor compartment 148. The concentrator 114 and the sample sensor compartment 148 are therefore considered to be contiguous and in fluid communication with each other.

Figure 4C:
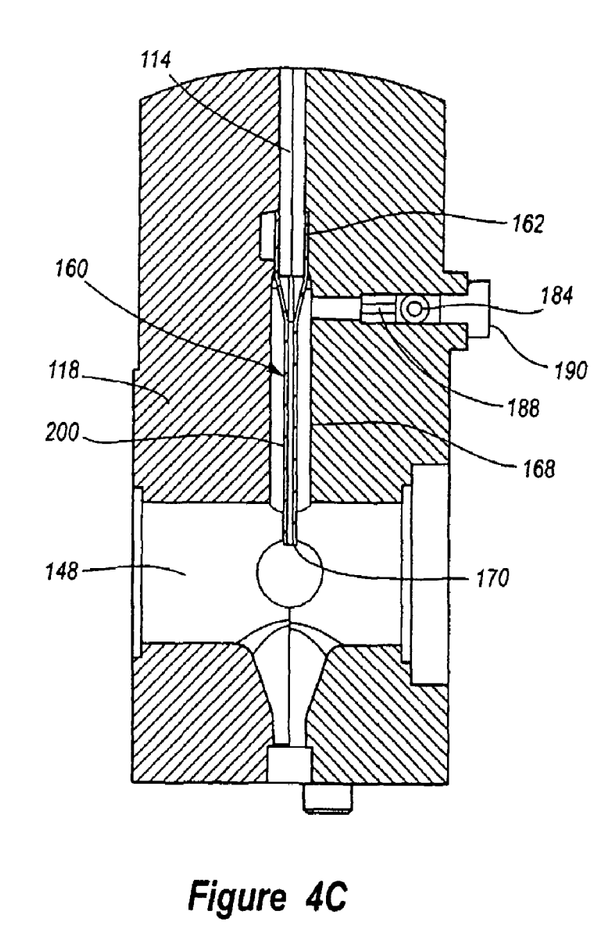
FIG. 4C is an enlarged partially cut-away cross-sectional side view of a sample sensor compartment as indicated by region 4C in FIG. 4B.
Figure 4D:
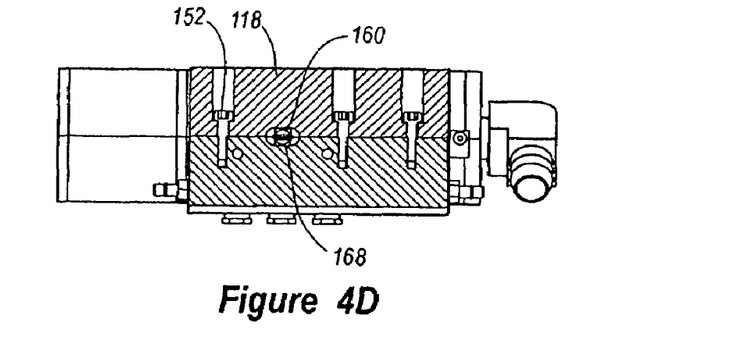
FIG. 4D is a cross-sectional bottom end view of the of the integrated particle detection apparatus of FIG. 4A as viewed from the cross-sectional plane 4D-4D.

Referring to FIGS. 4C and 4D, the sample air stream flows from the concentrator 114 into the upper end 162 of the sample nozzle 160. The flow of the sample air stream through an elongated portion 200 of the sample nozzle 160 is typically laminar. Surrounding the elongated portion 200 of the sample nozzle 160 is the sheath nozzle 168 which may be machined into the housing 118. Clean air flow may enter the particle detection apparatus through a flow manifold port 184 that is not restricted through the presence of a flow manifold plug 190.

The clean air flow then passes through the sheath flow orifice 188. The sheath flow orifice 188 regulates the volumetric sheath flow rate to a desired value. After the clean air passes through the sheath flow orifice 188, it enters into the sheath nozzle 168 which, according to the embodiment depicted, encompasses the sample nozzle 160. The sheath nozzle 168 has a length sufficient to "straighten" the sheath flow prior to entering the sample sensor compartment 148.

The sheath flow then enters into the sample sensor compartment 148 along with the particle-laden air sample that is delivered by the sample nozzle 160. The sheath flow helps control the shape of the particle-laden flow as it exits through the lower end 170 of the sample nozzle 160. The sheath flow also may help prevent optical surfaces from being coated with particles from the particle-laden flow.

Figure 5A:
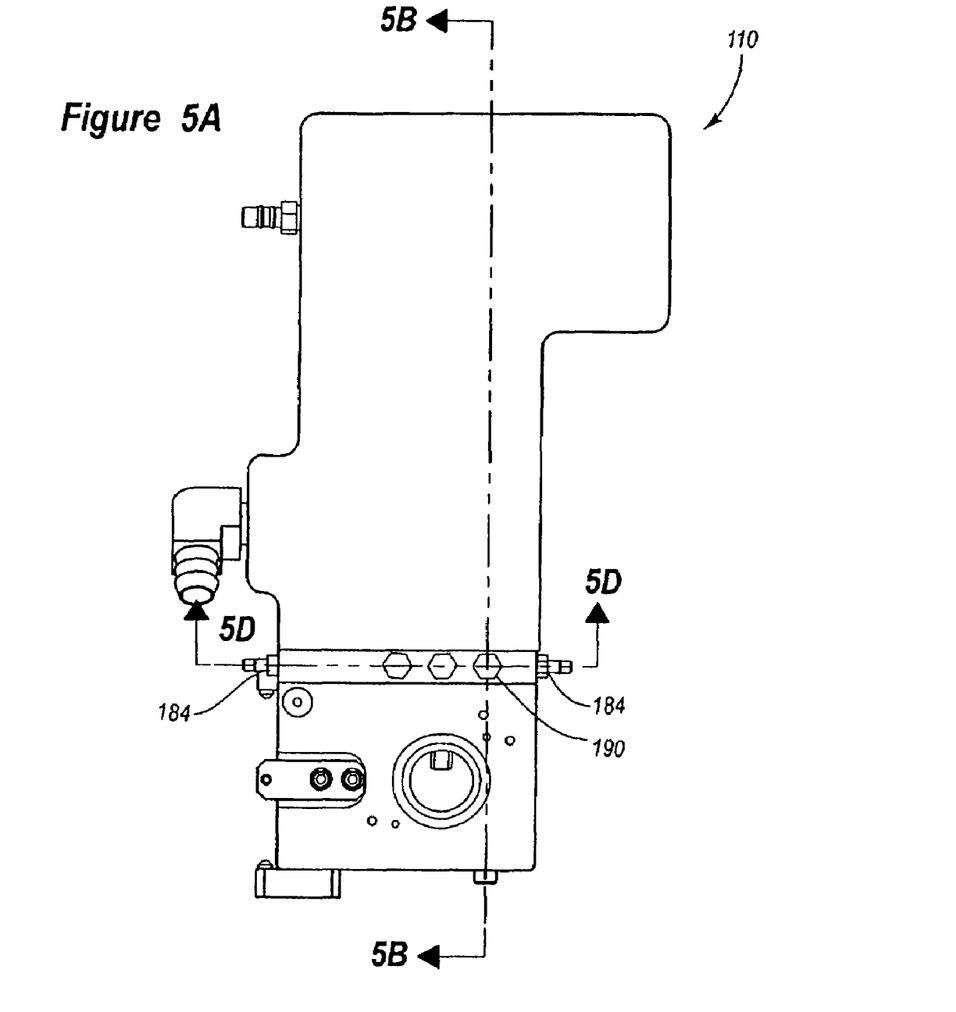
FIG. 5A is an alternative side elevation view of the integrated particle detection apparatus of FIG. 4A.

FIG. 5A illustrates the integrated particle detection apparatus 110 of FIG. 1 from an alternative side elevation view. Plane 5B-5B extends through the length and depth of the particle detection apparatus 110 and passes through a flow manifold port (as obscured by a flow manifold plug 190) and an internal purge flow orifice and purge flow port (not shown). Plane 5D-5D extends through the width and depth of the particle detection apparatus 110 and passes through an integrated flow manifold (not shown) and flow manifold ports 184 (some of which are obscured by flow manifold plugs 190). Plane 5D-5D also passes through the internal sample and sheath nozzles (not shown).

Figure 5B:
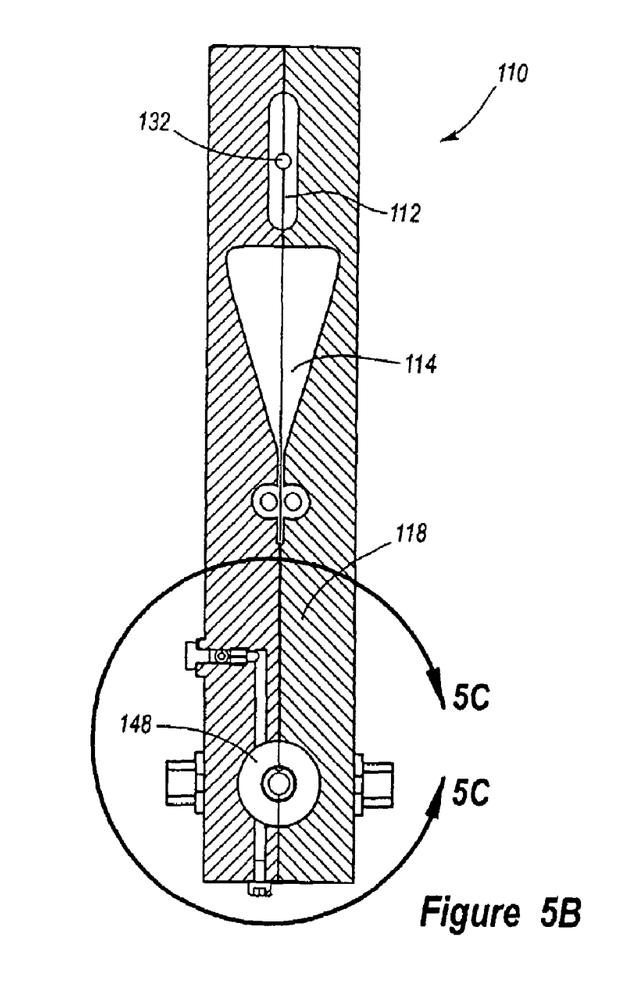
FIG. 5B is a cross-sectional side elevation view of the integrated particle detection apparatus of FIG. 5A as viewed from the cross-sectional plane 5B-5B.

FIG. 5B represents the particle detection apparatus 110 of FIG. 5A as illustrated from a side cross-sectional view along the plane 5B-5B. From this vantage point a portion of the scalper 112 and the scalper exhaust 132 are visible. A portion of the concentrator 114 and the sample sensor compartment 148 are also in view. The scalper 112, concentrator 114, and sample sensor compartment 148 are all formed in and defined by the housing 118 of the particle detection apparatus 110.

Figure 5C:
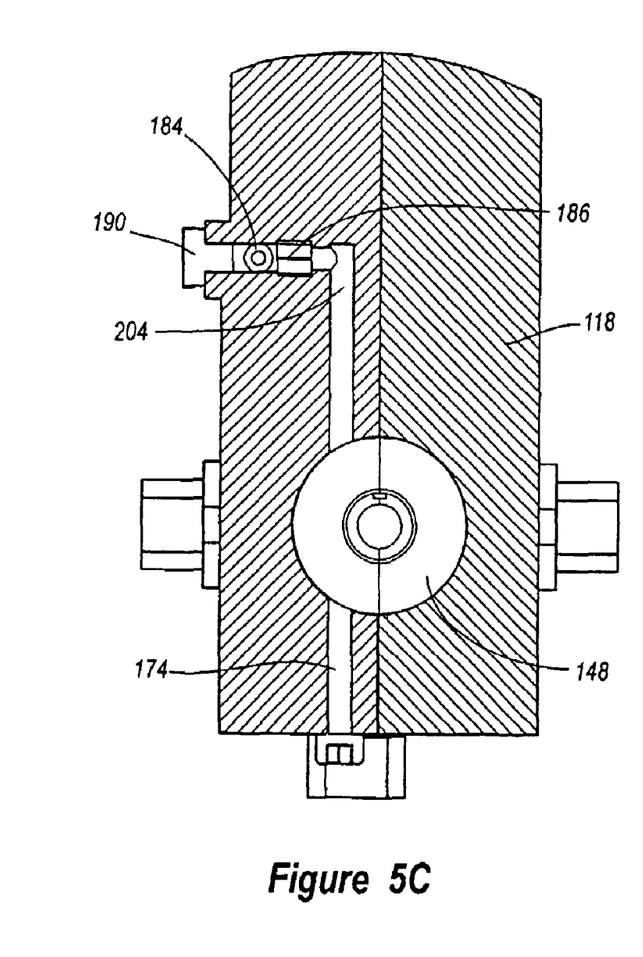
FIG. 5C is an enlarged partially cut-away cross-sectional side view of the integrated particle detection apparatus of region 5C in FIG. 5B.
Figure 5D:
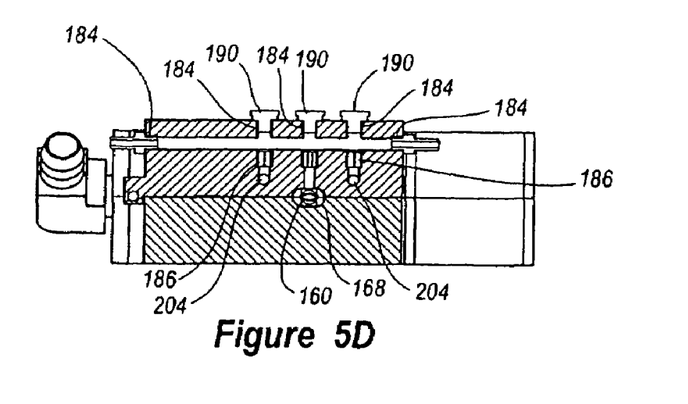
FIG. 5D is a cross-sectional bottom end view of the integrated particle detection apparatus of FIG. 5A as viewed from the cross-sectional plane 5D-5D.

Referring to FIGS. 5C and 5D, the particle detection apparatus 110 includes a flow manifold 202 that is integrated into the apparatus housing 118. Clean air may enter into the integrated flow manifold 202 through flow manifold ports 184 that are not obstructed by flow manifold plugs 190. Purge flow enters the sample sensor compartment 148 by initially passing through purge flow orifices 186. The purge flow orifice 186 may reduce the purge flow rate to a desired value.

After passing through the purge flow orifice 186, the purge flow enters into purge flow ports 204 that may exist in the housing 118 alongside the sheath and sample nozzles 168, 160. Purge flow is typically turbulent when it enters the sample sensor compartment 148. Like the sheath flow, the purge flow helps prevent the optics from being coated with particles from the particle-laden sample air flow. The resulting mixture of sample, purge and sheath air flow may exit the particle detector apparatus through the sensor exhaust 174.

While specific embodiments and applications have been illustrated and described, it is to be understood that the invention is not limited to the precise configuration and components disclosed herein. Various modifications, changes, and variations which will be apparent to those skilled in the art may be made in the arrangement, operation, and details of the methods and systems disclosed herein without departing from the spirit and scope of the invention.

What is claimed is:

1. A particle detection apparatus for detecting particles in a sample air stream, comprising:
   a scalper configured to separate out particles within the sample air stream based on particle size;
   a concentrator configured to increase a concentration of particles in the sample air stream;
   a sensor configured to detect particles; and
   a sample nozzle configured to deliver the sample air stream from the concentrator to the sensor;
   wherein the scalper is fluidly contiguous with the concentrator and the concentrator is fluidly contiguous with the sensor.

2. The apparatus of claim 1, wherein the sensor is an induced fluorescence sensor system.

3. The apparatus of claim 1, wherein the sample nozzle has a position within a housing that is adjustable from an outside of the housing.

4. The apparatus of claim 1, further comprising a sheath nozzle formed within the housing concentric with the sample nozzle.

5. The apparatus of claim 1, wherein the scalper is configured to remove particles larger than about ten microns in diameter from the sample air stream.

6. The apparatus of claim 1, wherein the concentrator is configured to remove particles smaller than about one micron in diameter from the sample air stream.

7. A particle detection apparatus for detecting particles in a sample air stream, comprising:
   a scalper that separates out particles within the sample air stream that are larger than a defined maximum size limit;
   a concentrator that increases a number of particles by volume in the sample air stream;
   a sample sensor compartment where fluorescence of sample particles occurs; and
   a housing comprising removable pieces providing access to an interior of the scalper, the concentrator, and the sample sensor compartment;
   wherein the scalper, concentrator and sample sensor compartment are in fluid communication with each other and are defined by the housing.

8. The apparatus of claim 7, wherein the concentrator separates out particles within the sample that are smaller than a defined minimum size limit.

9. The apparatus of claim 8, wherein the maximum size limit is about 10 microns in diameter and the minimum size limit is about 1 micron in diameter.

10. The apparatus of claim 7, further comprising a sealing member that provides a seal between the removable pieces when the removable pieces are joined together.

11. The apparatus of claim 7, further comprising a flow manifold having flow passages integrated in the housing.

* * * * *

UNITED STATES PATENT AND TRADEMARK OFFICE
CERTIFICATE OF CORRECTION

PATENT NO. : 7,659,523 B1  Page 1 of 1
APPLICATION NO. : 11/529114
DATED : February 9, 2010
INVENTOR(S) : Warrick et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 685 days.

Signed and Sealed this

Thirtieth Day of November, 2010

David J. Kappos
*Director of the United States Patent and Trademark Office*